United States Patent [19]
Hurson

[11] Patent Number: 5,525,314
[45] Date of Patent: Jun. 11, 1996

[54] SURGICAL TOOL CONTAINER SYSTEM

[75] Inventor: Steven Hurson, Yorba Linda, Calif.

[73] Assignee: Bausch & Lomb Incorporated, Rochester, N.Y.

[21] Appl. No.: 312,345

[22] Filed: Sep. 26, 1994

[51] Int. Cl.$^6$ .............................. A61L 2/00; B65D 85/20; A61G 15/16
[52] U.S. Cl. .................... 422/300; 422/297; 206/369; 206/379; 433/77; 211/69
[58] Field of Search ...................... 206/369, 379; 433/50, 51, 77; 211/69; 422/297, 300

[56] References Cited

U.S. PATENT DOCUMENTS

| | | | |
|---|---|---|---|
| 470,567 | 3/1892 | Hitch | 211/69 X |
| 1,451,806 | 4/1923 | Baldridge | 211/69 X |
| 1,519,614 | 12/1924 | Heck | 211/69 X |
| 2,971,637 | 2/1961 | Simons | 206/369 |
| 3,049,946 | 8/1962 | Schelke | 211/69 X |
| 3,102,637 | 9/1963 | Scholl | 211/69 |
| 4,032,008 | 6/1977 | Vecchiarelli | 206/379 |
| 4,253,830 | 3/1981 | Kazen et al. | 433/77 |
| 4,397,395 | 8/1983 | McKelvey | 211/69 |
| 4,503,972 | 3/1985 | Nelligan et al. | 206/379 |
| 4,736,838 | 4/1988 | Nakata et al. | 206/214 X |
| 4,762,688 | 8/1988 | Berry | 422/310 |
| 4,770,297 | 9/1988 | Chang | 206/379 |
| 4,922,603 | 5/1990 | Kosmowski | 211/69 X |
| 4,959,199 | 9/1990 | Brewer | 422/300 |
| 5,004,103 | 4/1991 | Connors et al. | 211/69 X |
| 5,071,346 | 12/1991 | Domaas | 433/300 X |
| 5,099,992 | 3/1992 | Heimreid | 206/366 |
| 5,172,810 | 12/1992 | Brewer | 206/369 |
| 5,174,453 | 12/1992 | Stoeffler | 206/570 |
| 5,188,242 | 2/1993 | Smith | 211/69 |
| 5,320,223 | 6/1994 | Allen | 206/372 |
| 5,358,112 | 10/1994 | Gardner | 211/69 X |
| 5,368,161 | 11/1994 | Plais | 211/69 X |

*Primary Examiner*—Robert J. Warden
*Assistant Examiner*—E. Leigh Dawson
*Attorney, Agent, or Firm*—Katherine McGuire; Craig E. Larson

[57] ABSTRACT

A surgical tool container system for the organization, sterilization, storage and presentation of a group of surgical instruments for selection and retrieval by a medical practitioner during a surgical procedure. The container system includes an outer case having separable base and lid portions with a tool-holding tray removably inserted within the base portion of the case. The tray is provided with a plurality of holes formed therethrough and wherein a respective plurality of elastomeric grommets are fixed to the tray. Each grommet includes an axially extending bore wherein the shank of a surgical tool may be inserted and frictionally engaged in a generally upright orientation with respect to the tray. The grommets removably secure the tools in their original positions within the container regardless of container orientation, yet also permit the quick and easy one-hand retrieval of a tool from the container during a surgical procedure, as well as equally quick and easy replacement of the tool within the container for subsequent sterilization and use cycles.

7 Claims, 7 Drawing Sheets

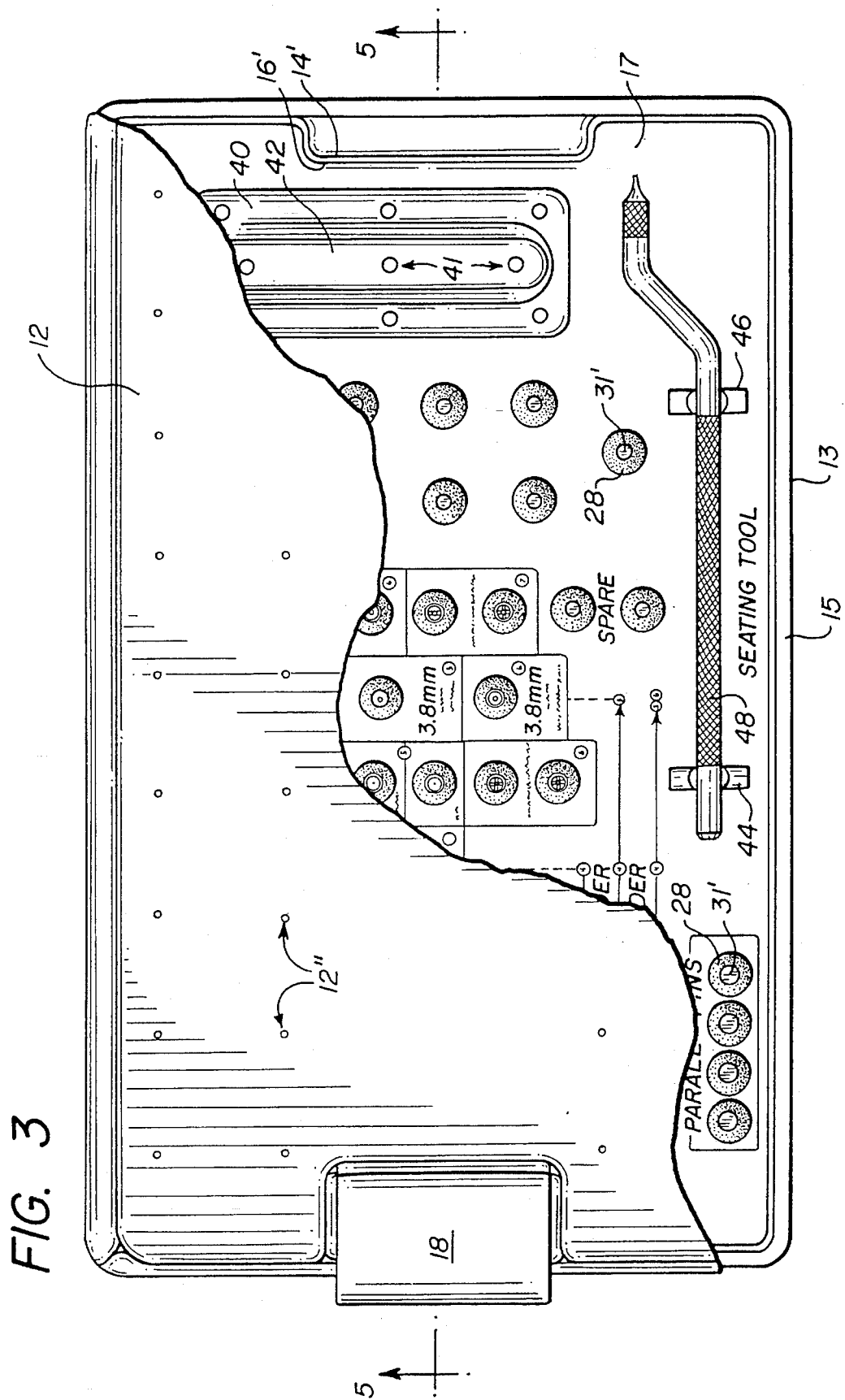

SURGICAL TOOL CONTAINER SYSTEM

BACKGROUND OF THE INVENTION

The present invention relates to container systems for tools and, more particularly, to a surgical container system for the organization, sterilization, and safe storage of delicate surgical instruments such as dental implantation tools (e.g., burrs and insertion wrenches).

Many surgical procedures require a specific, specialized group of surgical tools with any one procedure potentially requiring anywhere from just a few to literally dozens of individual tools. The tools must be sterilized and presented at the surgical site in a manner facilitating quick selection and retrieval of a needed tool by the medical practitioner during the surgical procedure. This is especially true in the dental arts, where many dental instruments are typically used in quick succession during one procedure. For example, a dental implant procedure normally requires the sequential use of several dental burrs (i.e., drills) of increasingly larger diameter, in addition to the intermediate and/or subsequent use of other implant tools (e.g., implant component insertion and extraction tools).

Container systems have been developed in the past which organize, sterilize, store and present a specific group of tools for a dental or other surgical procedure, all in the same container. In this regard, it is normally intended that the surgical tool container system organize a group of tools in a manner allowing the medical practitioner to retrieve the needed tools directly from the container during the surgical procedure. Examples of such containers may be seen in U.S. Pat. Nos. 5,172,810 and 4,959,199, both issued to Brewer on Dec. 22, 1992 and Sept. 25, 1990, respectively. Unfortunately, these as well as other prior container systems of their kind have given little attention to at least two very important considerations of such containers: 1) securing the tools in the container in a manner substantially preventing the accidental dislodgment of the tools from their original place within the container regardless of container orientation; 2) the ease by which a medical practitioner can select and then remove the needed tool from a group of tools within the container during a surgical procedure.

Regarding no. 1 above, during normal handling the container is many times inverted from its correct orientation, thus potentially disturbing the organization of the tools within the container. Should this occur, valuable time is spent on re-organizing the tools within the container prior to the surgical procedure, and hopefully without the need for re-sterilization should some of the tools fall entirely out of the container. The container thus preferably includes means to securely retain the tools in their organized position within the container, regardless of the orientation of the container.

Regarding no. 2 above, the medical practitioner needs to be able to select and remove the needed tool from the container fairly quickly and easily, and advantageously with the use of a single hand.

Since the tools are sterilized in the same container in which they are stored and used in surgery, the container must be very durable so as to be able to withstand repeated sterilization cycles and handling. While the container must be durable and include features to securely retain the tools in their position within the container, those features must not conflict with the need for quick identification and retrieval of a tool from the container. Also, once the surgical procedure is finished, the tools must be replaced in their original positions within the container. Thus, it is furthermore desirable that the features which permit the secure retention of the tools within the container also permit quick and easy replacement of those same tools back in their original positions in the container. These features provide a container system in which the group of tools may be quickly reorganized for subsequent sterilization, storage and use cycles.

SUMMARY OF THE INVENTION

The present invention meets the above needs by providing a surgical tool container system which organizes, sterilizes, and presents a specific group of tools for a surgical procedure, all in the same container. The container system further includes novel features designed to removably yet securely retain the individual tools in their organized positions within the container regardless of container orientation. Additionally, the container system includes features for facilitating a medical practitioner's quick identification of the correct tool for a given task from a group of tools held in the container, as well as providing a container which is extremely durable and able to withstand repeated sterilization cycles. The surgical tool container system of the present invention meets each of the above needs while also meeting the high aesthetic standards required in a state-of-the-art, professional medical setting.

More particularly, the container system of tile present invention generally comprises an outer case divided into separable top and bottom halves, and a tool holding tray which is removably inserted and held within the bottom half of the outer case. During storage and sterilization, the top half is secured to the bottom half of the case in complete covering relation to the tool holding tray. During a surgical procedure, the top half is removed from the bottom half of the case thereby exposing the tool holding tray and tools held thereon for selection and retrieval by the medical practitioner during surgery. The outer case is also provided with a plurality of vent holes wherethrough fluids may pass to reach the tools held on the inner tray during sterilization. The container may also be sterilized by known dry sterilization methods if desired. During sterilization and storage, the case is protectively placed within a sterilization bag in accordance with accepted sterilization and storage practice of surgical instruments.

As mentioned above, the tool holding tray is designed to organize and removably yet securely retain the individual tools used in a particular surgical procedure regardless of the container orientation. Additionally, the tray of the container system presents the tools to the medical practitioner in a manner greatly facilitating the identification and retrieval of the correct tool for a given task from the group of tools held on the tray during a surgical procedure. These design objectives are accomplished with the container system of the invention by the provision of a plurality of elastomeric grommets which are fixedly secured to the planar surface of the tray through a respective plurality of holes formed in a predetermined array pattern in the tray. The grommets are each configured with a central bore extending entirely therethrough and wherein a surgical tool may be inserted and securely yet removably retained in an upright fashion generally perpendicular with respect to the planar surface of the tray. A plurality of annularly spaced, axially and radially extending ribs are formed on tile inner surface of the bore of the grommet in a fashion permitting secure retention of the tool therein, yet also permitting easy retrievably of the tool using a minimum of manual force. The ribs also form longitudinal aeration channels therebetween for effective sterilization of a tool retained thereby.

Identical tools of slightly different sizes may be included in the same group of tools held on the tray. Accordingly, grommets having bores of varying diameters may be provided on the same tray. Additionally, the difference in sizes between the same type tool is many times so small that the tools are practically indistinguishable from one another without direct physical measurement. Since direct physical measurement of the individual tools is impractical during a surgical procedure, the presence of many tools of slightly different size on the same tray makes it difficult for the medical practitioner to quickly select the correct tool from the tray. To facilitate the identification and selection process, the tool holding tray is further provided with identifying indicia imprinted thereon which not only identifies each tool held in the tray, but also indicates the correct subgroup of tools used in a particular type of procedure, and the correct sequence of use of that sub-group. The tools and respective grommets and indicia are furthermore arranged on the tray in a pattern greatly enhancing the above-described tool identification and selection process.

Since the grommets are designed to hold tools of a particular size and configuration, and especially tools having a cylindrical shank portion for insertion into the bore of a grommet, the tray may be provided with additional tool holding means for accommodating tools of odd sizes and configurations. For example, the tray may be additionally provided with a recessed portion forming a cavity which includes a removable cover held over the cavity by the top half of the case in the closed condition of the case. Optionally, brackets and/or clips may also be used to hold tools having a length greater than the distance between the upper surface of the tray and the inner surface of the top half of the case. In this instance, the longer tools may be placed in a horizontal position relative to the tray, and secured thereon by the brackets and/or clips in which they are inserted.

BRIEF DESCRIPTION OF THE DRAWINGS

FIG. 3 is a top plan view of the fully assembled container with the top half of the case shown partly broken away;

DETAILED DESCRIPTION OF THE PREFERRED EMBODIMENT

Figure 1:
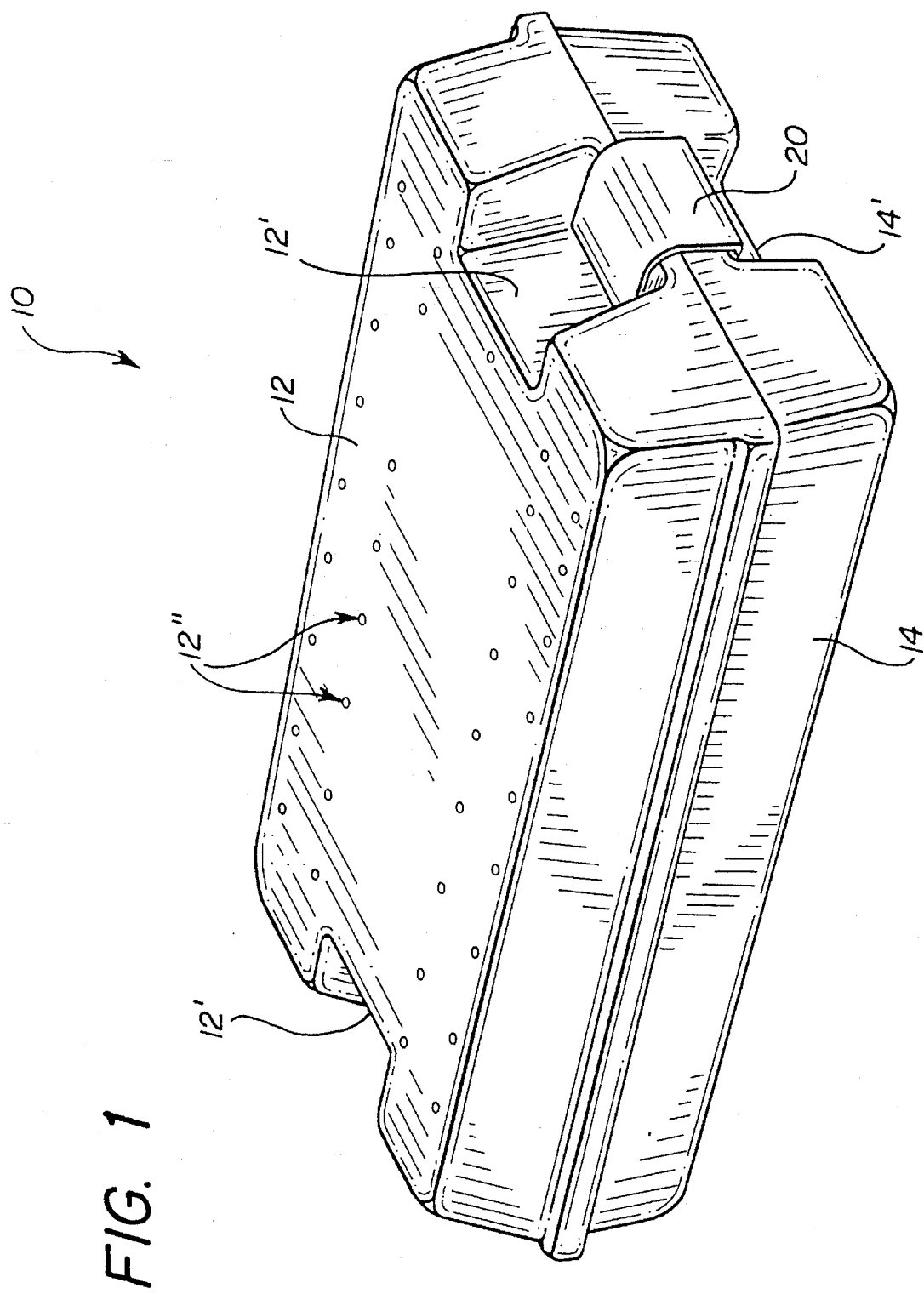
FIG. 1 is a perspective view of the tool container system in the fully assembled, closed condition of the container.

Referring now to the drawings, there is seen in the various Figures a surgical tool container system designated generally by the reference numeral 10. Container system 10 is designed for organizing, sterilizing, and storing a specific group of surgical tools, all in the same container 10. Additionally, container system 10 organizes and presents the tools in a manner allowing the medical practitioner to select and retrieve a needed tool directly from container 10 during the surgical procedure. As described in detail below, means are provided for removably yet securely retaining the tools in an organized fashion in container 10 regardless of container orientation. Furthermore, means are also provided for facilitating a medical practitioner's identification and retrieval of the correct tool, as well as the correct sequence of use of a sub-group of the tools needed for a particular task from the container 10. It is noted that while container system 10 is designed to facilitate the tool identification and retrieval process, it must also be used in accordance with accepted surgical protocols for a given procedure which takes into account the patient's case study as well as the practitioner's surgical knowledge and style. Container system 10 is thus not intended to completely supplant the practitioner's tool identification and selection process, but rather facilitate it in a manner making for a more efficient surgical procedure.

Container system 10 generally comprises an outer case having separable top lid and bottom base halves 12 and 14, respectively, and a tool holding tray 16 which is removably secured in base 14. As seen, top lid 12, bottom base 14, and inner tray 16 are preferably of generally rectangular configuration, with each including respective indented portions 12', 14', and 16' on opposite sides thereof, respectively, for the placement of container closure and carrying means. In this respect, top lid 12 includes first and second, resilient spring clasps 18 and 20 at opposite indented portions 12', respectively, which engage tile ledges formed at respective, opposite indented portions 14' on bottom base 14 when the two halves are attached together as seen best in FIGS. 1 and 5. The resilient nature and curved configuration of clasps 18 and 20 permit the easy attachment and removal of lid 12 from base 14. Particularly, clasps 18 and 20 snap into engagement with the ledges formed by opposite recessed ledge portions 14' of base 14 upon pressing lid 12 thereagainst, and pulling clasps 18 and 20 away from base 14 allows lid 12 to be freely and completely lifted from base 14. Top lid and bottom base portions 12 and 14 further include a respective plurality of small vent holes 12" and 14" formed therethrough for tile passage of fluids during sterilization of tile tools which are secured to tray 16 as described below. It is intended that during sterilization and storage periods, container system 10 be protectively placed within a sterilization bag (not shown) in accordance with accepted surgical instrumentation sterilization practice.

Figure 2:
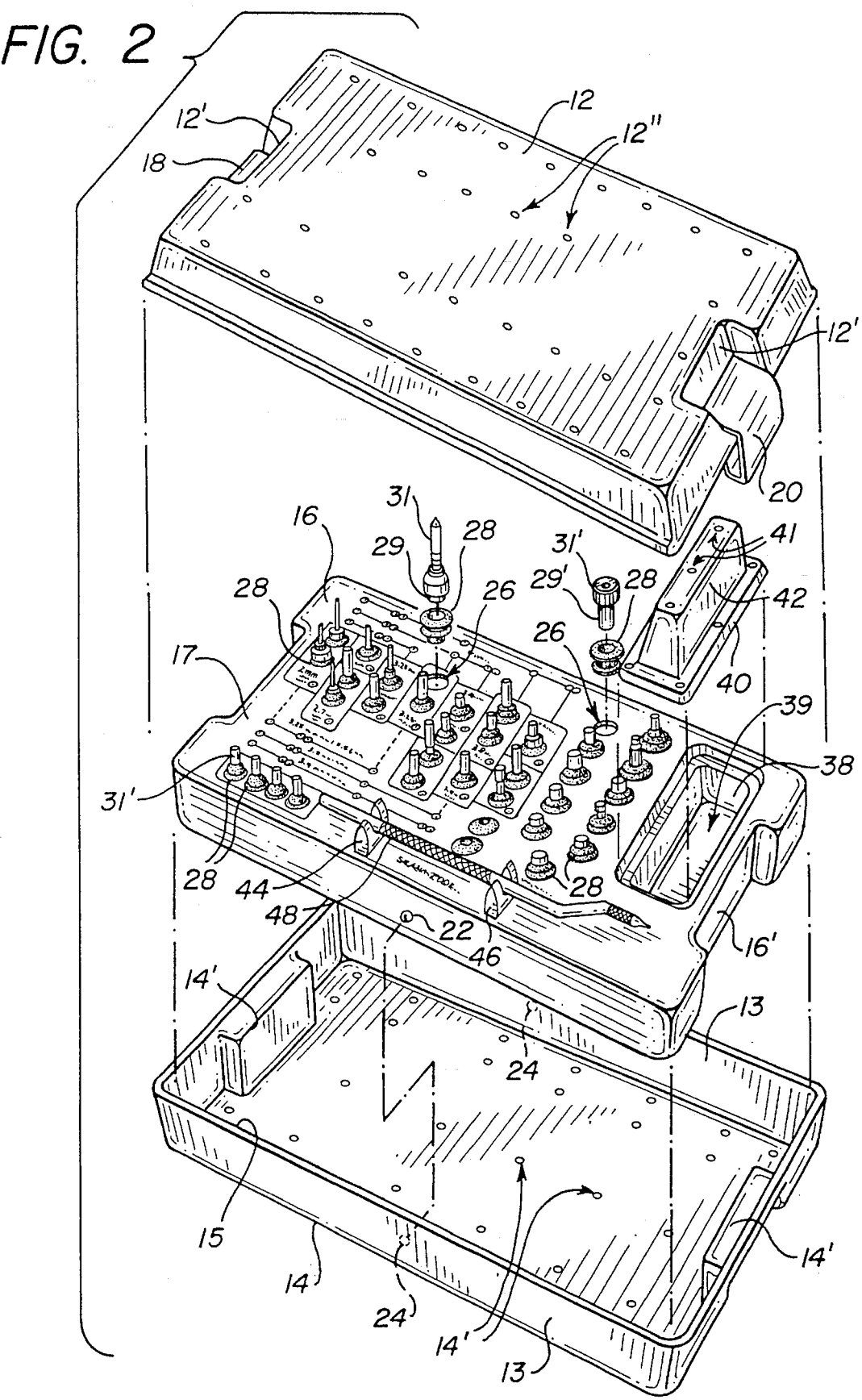
FIG. 2 is an exploded, perspective view of the tool container system showing the inner tray thereof holding a group of surgical tools used in performing dental implant surgery.
Figure 5:
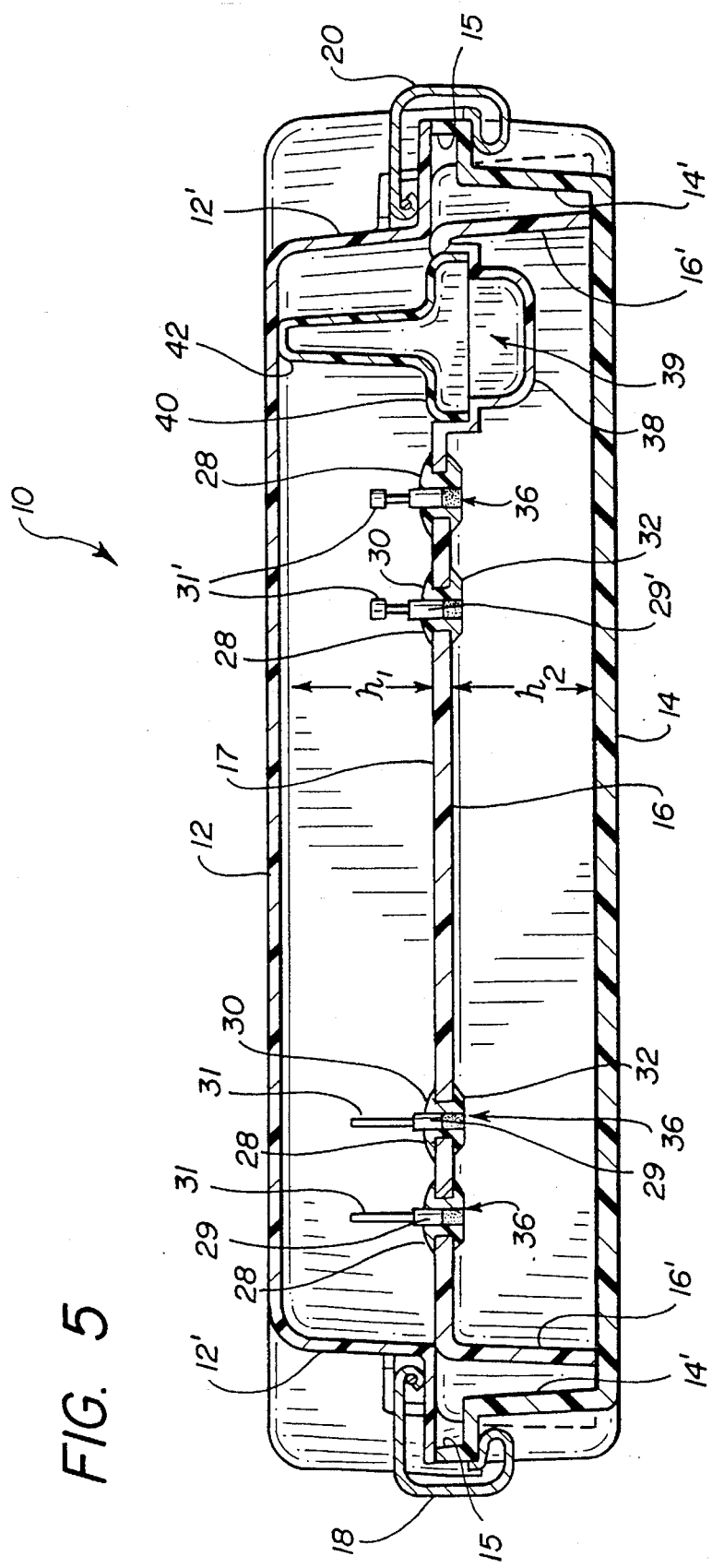
FIG. 5 is a cross-sectional view of the fully assembled container system as taken generally along the line 5—5 in FIG. 3.
Figure 6:
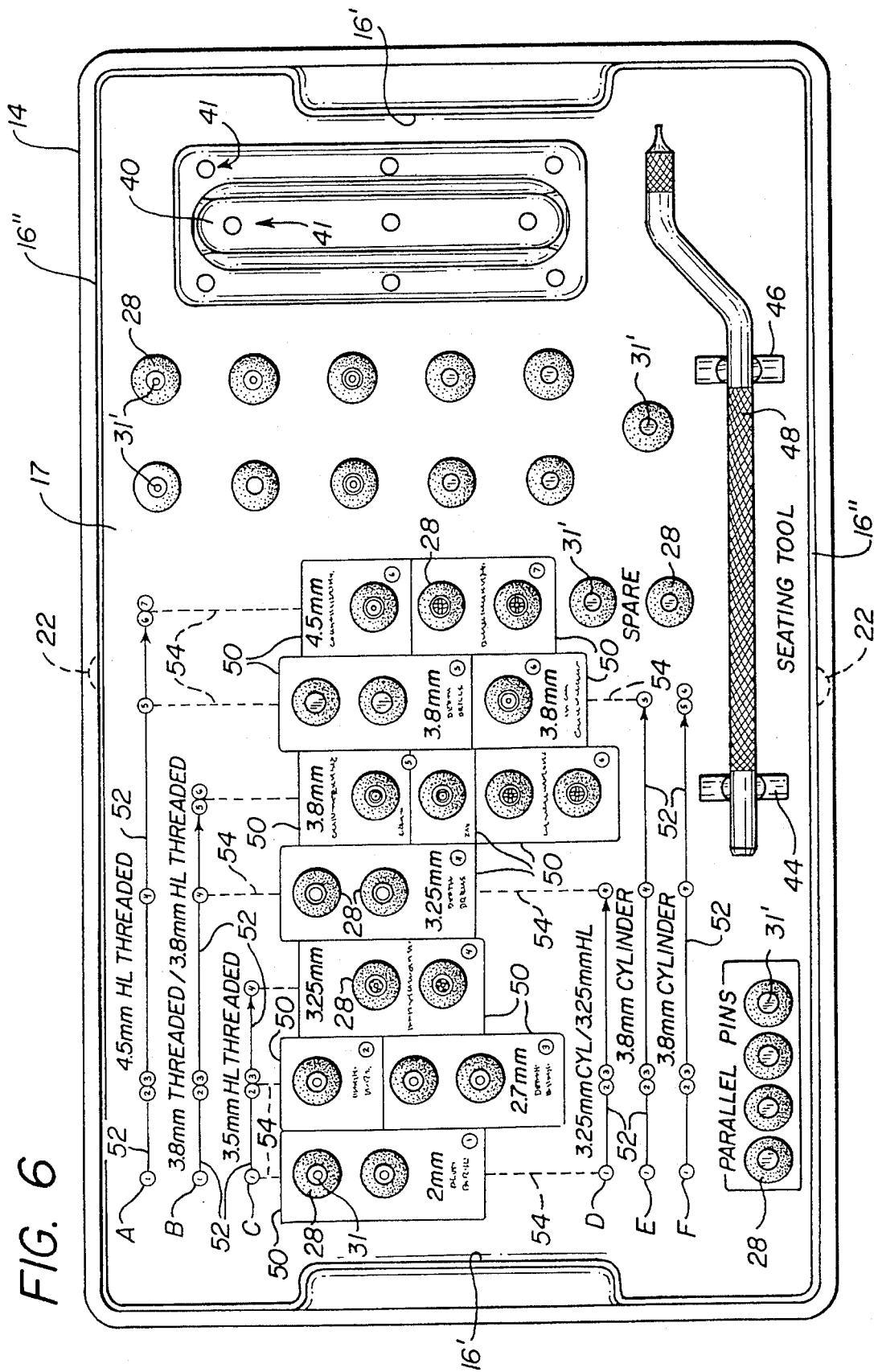
FIG. 6 is an enlarged, top plan view of the inner tray of the container system.

As seen best in FIGS. 2 and 6, inner tray 16 includes a pair of bosses 22 projecting from the outer surface of opposite side walls 16" thereof for snapping engagement with aligned recesses 24 formed on the inside surfaces of opposite side walls 13 of base portion 14. When tray 16 is fully inserted within base portion 14, the top planar surface 17 thereof lies approximately even with the top edge 15 of base portion 14, and open spaces having heights $h_1$ and $h_2$ are formed between tray 16 and the top wall of lid 12, and the bottom wall of base 14, respectively (FIG. 5). As described below, means are provided to removably secure a group of surgical tools to the upper planar surface 17 of tray 16 in a particular array pattern especially adapted for the particular group of tools described herein. In this respect, the removability feature of tray 16 allows other trays designed for different groups of tools to be inserted within base portion 14 as needed, thereby increasing the usability and versatility of container system 10.

Description will first be directed to the means by which a group of surgical tools may be removably secured to the tray. As seen in FIG. 2, a group of surgical tools for performing dental implant surgery is shown removably secured to the upper planar surface 17 of tray 16 in the specific manner described below. Although the invention is described and shown therein for use in combination with a group of surgical tools for dental implant surgery, it is understood that container system 10 could be used with other types of surgical tools having sizes and configurations somewhat similar to the dental implant tools described and shown herein.

Figure 4A:
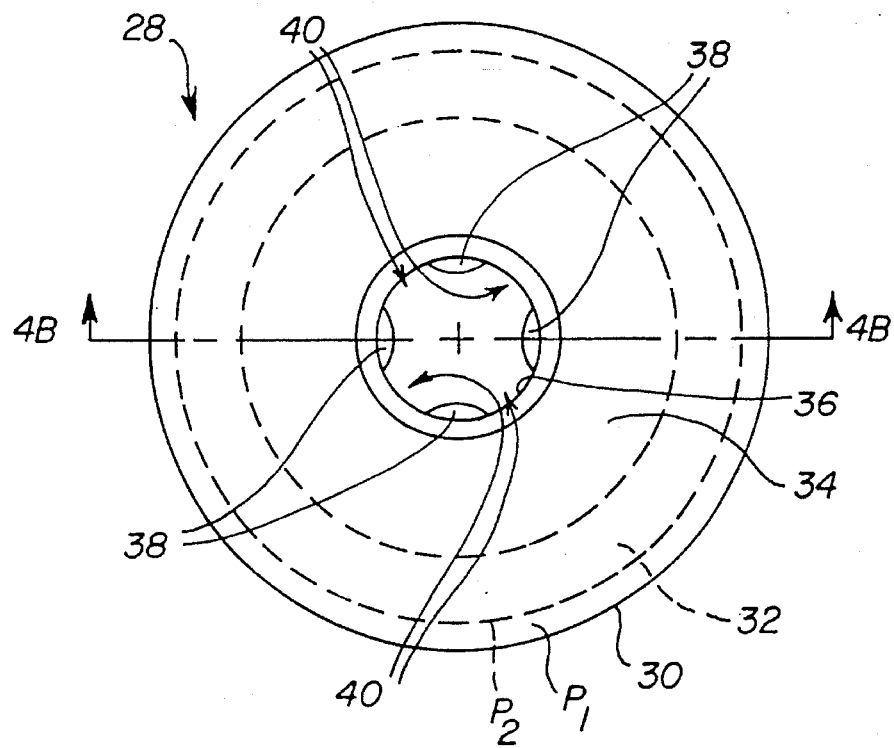
FIG. 4A is a top plan view of one of the tool holding grommets which are fixed to the inner tray of the container system.
Figure 4B:
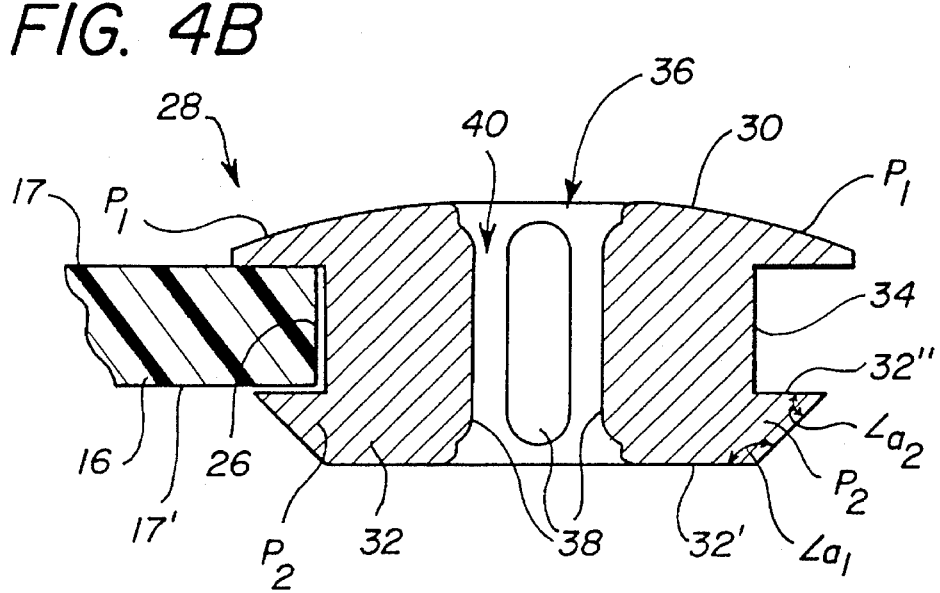
FIG. 4B is a cross-sectional view as taken along the line 4B—4B in FIG. 4A, and further showing the manner of attachment thereof to the tray (fragmented, left side only)

As seen best in FIGS. 2, 5 and 6, the upper planar surface 17 of tray 16 is provided with a plurality of circular holes 26 formed therethrough in a predetermined array pattern.(The specific pattern illustrated in the drawing facilitates the tool identification and retrieval process of the specific group of tools herein described, and will be discussed in more detail later in connection therewith). A respective plurality of elastomeric grommets 28, one of which is seen in enlarged detail in FIGS. 4A and 4B, are fixedly secured within a respective hole 26 to removably secure surgical tools to tray 16. Grommets 28 are seen to be of generally cylindrical configuration, having top and bottom annular portions 30 and 32, respectively, interconnected by a cylindrical segment 34 extending therebetween. A center bore 36 extends entirely axially through grommet 28 wherein the shank portion 29 of a tool 31 may be removably inserted and held in frictional engagement therewith (FIG. 2). In this regard, a plurality of longitudinally extending ribs 38 are formed in radially spaced relation on the inside surface of bore 36, thereby forming a respective plurality of longitudinally extending aeration channels 40 therebetween wherethrough fluids may pass to sterilize the shank portion 29 of the tool 31 which extends within and is frictionally engaged by ribs 38 in bore 36.

While the upper surface of top portion 30 is smoothly convex and is relatively thin at the perimeter portion p which extends radially of cylindrical segment 34, bottom portion 32 is of generally trapezoidal cross-section with the perimeter portion $p_2$ thereof tapering radially outwardly toward top portion 30, forming an obtuse angle $a_1$ with the bottom surface 32' thereof, and an acute angle $a_2$ with the top surface 32" thereof which itself intersects cylindrical portion 34 at a right angle. This trapezoidal configuration of bottom portion 32 allows bottom portion 32 to be forced through a hole 26, the diameter of which is larger than the outer diameter of the bottom surface 32' thereof, but less than the outer diameter of the top surface 32" thereof. Since grommet 28 is elastomeric and thus resilient as described, bottom portion 32 deforms to fit through hole 26, and thereafter immediately reforms such that the perimeter of hole 26 lies in immediately adjacent relationship to cylindrical portion 34, and the perimeter portions $p_1$ and $p_2$ of top and bottom portions 30 and 32, respectively, lie in close, abutting relationship to the top and bottom surfaces 17 and 17' of tray 16, respectively. As such, grommets 28 are substantially fixedly secured in a respective hole 26 in tray 16.

As previously described, in the fully assembled, closed condition of the container system 10 seen in FIG. 5, spaces having heights $h_1$ and $h_2$ are created both above and below tray 16 between the top lid 12 and bottom base 14, respectively. As such, the shank portions 29 and 29' of dental burrs 31 and other dental implant tools 31', respectively, may be inserted into the bore 36 of a respective grommet 28. With the shank portions 29 and 29' of the tools frictionally engaged by the ribs 38 of a respective grommet 28, the tools 31 and 31' are securely yet removably engaged by their respective grommet 28 to tray 16. The force of the frictional engagement between the grommet 28 and tool 31, 31' is such that the tool will not accidentally dislodge from the grommet regardless of container orientation, yet may be easily removed therefrom upon manually pulling the tool from its grommet. Also, since the length of the tools 31, 31' are less than the height $h_1$ of the space between the tray 16 and lid 12, the tools may assume a generally upright orientation which is generally perpendicular to the top surface 17 of the inner tray 16. It will be appreciated that this upright orientation of the tools permits a tool to be easily grasped with a single hand and pulled free from the grommet in which it is held.

The majority of dental implant tools are small and include a shank portion such as 29 and 29' which permit the insertion and engagement thereof into the bore 36 of a grommet 28. However, some dental implant tools are of odd sizes and configurations which cannot fit within the bore 36 of a grommet 28 and/or cannot be accommodated in an upright fashion within the space between the tray 16 and lid 12. In this regard, alternate tool securing means are provided on tray 16 to accommodate tools of odd sizes and configurations. In particular, a recessed portion 38 may be formed in the top surface 17 of tray 16 thereby forming a cavity 39 of preferably rectangular configuration wherein miscellaneous dental tools (not shown) may be placed. A cover 40 is provided having a raised center portion 42 which is of a height causing the top lid 12 to firmly engage cover portion 42 in the closed condition of container system 12. As such, cover 40 encloses and maintains the contents of recessed cavity 39 inside cavity 39 regardless of container orientation. Cover 40 is further provided with a plurality of vent holes 41 for passage of fluids into cavity 40 during sterilization. Additional tool securing means may take the form of conventional, resilient finger brackets 44 and 46 which form spaced slots wherein the shaft of an elongated tool 48 having a height greater than $h_1$ (e.g., the dental implant seating tool shown in FIGS. 2 and 6) may be inserted and removably retained with tool 48 lying generally horizontal relative to tray surface 17.

As previously mentioned, grommets 28 are preferably arranged on tray 16 in a predetermined array pattern which is necessarily dictated, at least in part, by the particular group of tools being held on tray 16. The tools herein described, such as burrs 31 and auxiliary tools 31', 48, are part of a group of tools designed especially for dental implant surgery. Depending on the type and size of dental implant being surgically implanted into the patient's mouth, only a certain sub-group of the tools on tray 16 might be used for a given procedure. The tools and respective grommets have therefore been arranged on tray 16 in a predetermined pattern greatly facilitating the tool identification and selection process.

More particularly, as seen in FIG. 6, the grommets 28 are placed in a particular pattern on tray 16, and identifying indicia is imprinted upon the upper surface 17 of tray 16. The group of tools and respective grommets 28 positioned within the rectangular boxes 50 are dental burrs 31 for forming the hole (osteotomy) within the patient's jaw bone. These burrs 31 are further divided into six separate sub-groups by the indicia A–F according to the type of implant being inserted into the patient's mouth (i.e., "4.5 mm HL THREADED";"3.8 mm THREADED/3.8 mm HL THREADED"; and 3.25 mm HL THREADED" seen imprinted above the rectangular boxes 50; and "3.25 mm CYL/3.25 mm HL CYL"; 3.8 mm CYLINDER"; and 3.8 mm HL CYLINDER" seen imprinted below the rectangular boxes 50). Numerals and horizontal lead lines 52 indicate the correct sequence of the particular sub-group of tools, while vertical dashed lines 54 indicate the exact tool to be used in the sequence. The numerals which indicate the sequence number of the tool in the sub-group are also imprinted directly adjacent the tool within the rectangular box 50 to further facilitate tool identification. Since dental burrs 31 are difficult to distinguish from each other because of their similar sizes and configurations, this indicia scheme and array pattern of the tools greatly facilitates a medical practitioner's identification and selection process of dental burrs 31 on tray 16 during a surgical procedure. Auxiliary dental implant tools 31' and 48 are arranged in side-by-side fashion to the right and below dental burrs 31 since they are relatively easy to distinguish from one another and therefore do not require any special indicia scheme. These auxiliary tools are used intermediate and/or subsequent to the use of dental burrs 31 during the implant procedure as will be explained more fully below. To understand the manner in which the indicia scheme and array pattern of dental burrs 31 and respective grommets 28 facilitate the identification and selection process, a couple of case examples of particular implant procedures using the tools are set forth and explained below.

CASE EXAMPLE 1

A practitioner is installing a 3.25 mm hexed implant (not shown), with the hexed portion thereof providing a non-circular surface for engagement with an implant insertion tool such as the 0.050 Hex Driver seen to the right of boxes 50 (the hexed projection also provides an anti-rotational feature when combined with the abutment component of the implant system, also not shown). Knowing that the abbreviation "HL" indicates a hexed component, the practitioner immediately identifies sub-group C as the correct sub-group of dental burrs needed to form the osteotomy having the required dimensions for effective installation of a 3.25 mm hexed implant. As previously mentioned, the tool identification process the present container system 10 provides is not intended to supplant a practitioner's medical knowledge of proper surgical protocols for performing a given surgical procedure. Rather, the container system 10 of the present invention provides means for facilitating the identification and selection process of the tools needed to perform a particular surgical task. In this regard, a practitioner would normally know that proper dental implant surgical protocol requires that a small diameter osteotomy is first formed, preferably using a disposable 1.5 mm twist drill, which is subsequently and gradually enlarged to form an osteotomy of the required dimensions. Since the 1.5 mm drill is disposable and not re-used, it is not placed within container system 10 and has therefore not been shown in the drawing.

Figure 7:
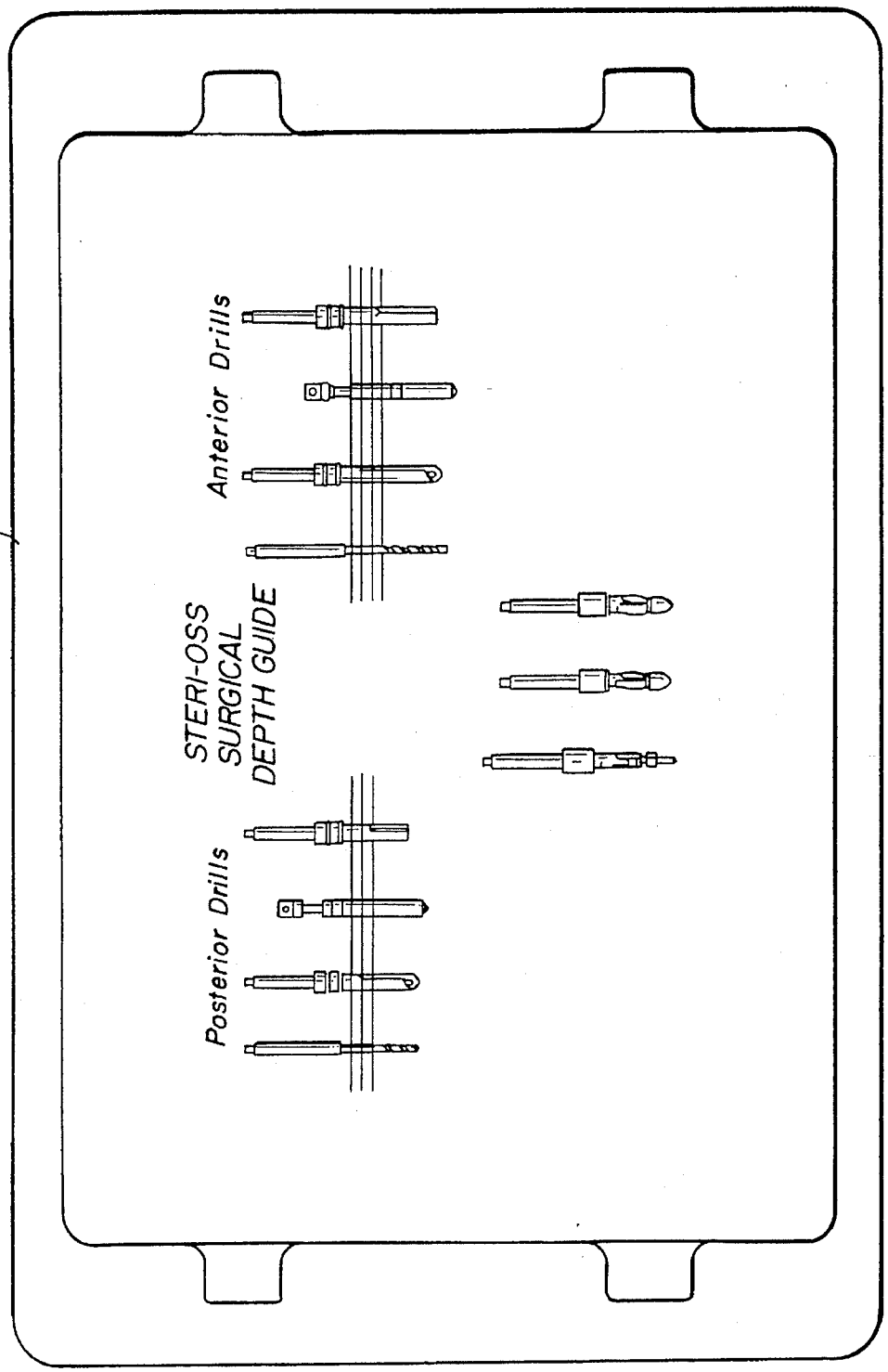
FIG. 7 is a plan view of the inside surface of the top lid of the outer case of the container system.

After the initial hole has been formed, the practitioner uses the tools in container system 10 to finish the preparation of the osteotomy and subsequent implant installation. The horizontal lead lines 52 in sub-group C indicates there are a total of four burrs 31 required to be used in sequential succession, with the dashed vertical lead lines 54 indicating the correct tool within that sub-group to be used at a given time. Beginning with number one in sub-group C, the dashed vertical line 54 leads to the first rectangular box 50 which encompasses two burrs 31 and respective grommets 28, which are further identified by indicia imprinted within the perimeter of box 50 as "2 mm PILOT DRILLS". The presence of two of the same tool in one rectangular box 50 indicates there are two of the same tool differing only in their lengths, with the longer of the two tools being used for drilling in the anterior region or the mouth, and the shorter being used for drilling in the posterior region of the mouth due to a minimum of clearance in that region. In container system 10, it is generally understood that the posterior drilling tools are positioned below the anterior tools, but some of the tools having separate anterior and posterior lengths are reproduced to scale on the inside of the top lid 12 as seen in FIG. 7 to allow for direct comparison if needed.

Following use of the 2 mm Pilot Drill, the practitioner follows the horizontal lead line 52 in sub-group C to the second tool in the sub-group which is indicated by vertical lead line 54 to be the Guide Drill (which also has the number two imprinted adjacent thereto within box 50). The Guide Drill is used to maintain concentricity of the osteotomy between the 2 mm Pilot Drill and the 2.7 mm Depth Drill which is listed as tool number three in sub-group C. Thus, subsequent to using the Guide Drill, the practitioner proceeds to the 2.7 mm Depth Drill which are reproduced on lid 12 for direct comparison of the posterior and anterior lengths provided in box 50 (if needed). Lastly, the horizontal lead lines 52 lead from tool number three to number four in sub-group C, with the vertical line 54 thereof leading to the 3.25 mm Threadformers (in both anterior and posterior lengths, also reproduced on lid 12). Following the use of the fourth tool in the sub-group, the final osteotomy profile is completed and ready to receive the 3.25 mm HL THREADED implant using the auxiliary tools 31' and 48 as required.

It may thus be realized that the tool identification and selection process is greatly facilitated by the particular arrangement of the tools on tray 16 which lead the practitioner from the left to the right of the tray 16, as well as the indicia imprinted thereon which identifies the correct sub-group of tools as well as their proper sequence of use for a particular implant procedure. The particular patient case study as well as practitioner style may result in slight deviations from the sub-group sequence just described. For example, in dense cortical bone, a threadformer is usually required such as the one labeled number four in sub-group C. In less dense bone, a threadformer might not be needed, in which case the practitioner would skip the use of the threadformer in the sub-group C sequence and proceed directly from the 2.7 mm drill to installation of the 3.25 mm implant. Also, intermediate use of an auxiliary tool may be required. For example, the parallel pins 31' seen in the bottom left corner of the tray 16 may be inserted into the osteotomy following use of the 2 mm Pilot Drill to check for proper orientation of the osteotomy. Again, these deviations are considered normal occurrences which are decided by the practitioner.

CASE EXAMPLE 2

A practitioner is installing a 3.25 mm cylindrical implant which is tapped into the osteotomy rather than threaded as are the threaded type implants. The practitioner immediately identifies sub-group D as the proper sub-group of tools needed to form an osteotomy for this type of implant (which is the same whether it is hexed or not as indicated by the indicia 3.25 mm CYL / 3.25 mm HL CYL). The indicia indicates to the practitioner that there are four burrs normally used to form the needed osteotomy for this implant type, and proceeds to number one in the sub-group following any initial drilling required with a disposable drill as previously described. It may be seen that the first three burrs in sub-group D are the same as that for sub-group C described above. However, it will furthermore be noticed that the threadformers are not used for installation of cylindrical type implants since they are not threaded into the osteotomy. The horizontal lead lines 52 therefore in this instance skip over the threadformers and lead to the 3.25 Depth Drills instead which also include the number four imprinted within the perimeters of the box 50 adjacent to the grommet 28 positioned therein. Following use of the 3.25 mm Depth Drill, the osteotomy is ready to receive the 3.25 mm cylindrical implant.

The remaining sub-groups of tools A, B, E, and F are used for installing their particular type of implant, and the process of tool identification and selection is substantially the same as that described in the case examples provided above.

The above case examples illustrate how the indicia on tray 16, as well as the arrangement of the tools and grommets which hold the tools, act to greatly facilitate both the identification and retrieval of a needed tool from the tray during a particular surgical procedure.

What is claimed is:

1. A surgical tool container system comprising:

a) an outer case including a base portion and lid portion movable between open and closed positions relative to one another;

b) a tray having opposite upper and lower planar surfaces, said tray secured within said base portion of said outer case, said lid portion extending in complete covering relating to said tray upper surface and defining a first space having a height $h_1$ therebetween when said base and lid portions are placed together in said closed position, and a second space having a height $h_2$ being defined between said tray lower surface and said base portion, said tray including a plurality of holes formed entirely through said upper planar surface to said lower planar surface and arranged in a predetermined array pattern on said tray; and c) a plurality of elastomeric grommets each having upper and lower annular segments interconnected by a cylindrical segment, each of said grommets being fixedly secured to said upper planar surface of said tray through a respective one of said plurality of holes with said cylindrical segment located in a respective said hole and said upper and lower annular segments lying in abutting relation to said upper and lower surfaces of said tray, respectively, adjacent said respective hole, said grommets further each including a bore having an inner bore surface extending entirely axially therethrough and wherein the shank of a surgical tool may be inserted and frictionally held thereby with said tool including portions thereof extending within said first space substantially perpendicular to said upper planar surface of said tray.

2. The container system of claim 1 wherein said elastomeric grommets each further include at least two annularly spaced, radially and axially extending ribs formed on said inner surface of said bore, said ribs frictionally engaging the shank of a tool inserted within said bore with a respective number of longitudinal aeration channels being defined between each of said ribs.

3. The container system of claim 1 wherein said upper and lower annular segments each have a diameter larger than said cylindrical segment, and said cylindrical segment has a diameter smaller than the diameter of a respective one of said holes in said tray whereby said grommet may be fixed to said tray with said cylindrical segment thereof extending through a said respective hole with said upper and lower annular segments of said grommet lying in abutting contact with said upper and lower surfaces of said tray, respectively, adjacent said respective hole.

4. The container system of claim 1 wherein said upper annular segment has a smoothly convex surface facing away from said tray, and said lower annular segment is of substantially trapezoidal cross-section tapering gradually outwardly toward said cylindrical segment, whereby said grommet may be fixedly secured to said tray by forcing said lower annular segment thereof through a respective said hole in said tray until said cylindrical segment extends entirely through said hole.

5. The container system of claim 4 wherein said elastomeric grommets each further include at least two annularly spaced, radially and axially extending ribs formed on the surface of said bore, said ribs frictionally engaging the shank of a tool inserted within said bore with longitudinal aeration channels being defined between each of said ribs.

6. The container system of claim 5 wherein said grommets each include four of said ribs which are equally annularly spaced from one another in said bore.

7. The surgical tool container system of claim 1 wherein said tray is removable from said base portion.

* * * * *

UNITED STATES PATENT AND TRADEMARK OFFICE
CERTIFICATE OF CORRECTION

PATENT NO. : 5,525,314
DATED : June 11, 1996
INVENTOR(S) : Steven Hurson

It is certified that error appears in the above-indentified patent and that said Letters Patent is hereby corrected as shown below:

In column 5, line 38, change "portion p" to -- portion $p_1$ --.

Signed and Sealed this

Eleventh Day of February, 1997

Attest:

BRUCE LEHMAN

Attesting Officer     Commissioner of Patents and Trademarks